(12) United States Patent
Johnson

(10) Patent No.: US 9,676,700 B2
(45) Date of Patent: Jun. 13, 2017

(54) PREPARATION OF FLUOROSULFONATE ESTERS AND ONIUM SALTS DERIVED THEREFROM

(71) Applicant: Trinapco, Inc., Oakland, CA (US)

(72) Inventor: Martin Reid Johnson, Piedmont, CA (US)

(73) Assignee: TRINAPCO, INC., Oakland, CA (US)

( * ) Notice: Subject to any disclaimer, the term of this patent is extended or adjusted under 35 U.S.C. 154(b) by 0 days.

(21) Appl. No.: 14/766,092

(22) PCT Filed: Feb. 11, 2014

(86) PCT No.: PCT/US2014/015859
§ 371 (c)(1),
(2) Date: Aug. 5, 2015

(87) PCT Pub. No.: WO2014/124456
PCT Pub. Date: Aug. 14, 2014

(65) Prior Publication Data
US 2015/0368182 A1 Dec. 24, 2015

Related U.S. Application Data

(60) Provisional application No. 61/765,560, filed on Feb. 15, 2013, provisional application No. 61/763,087, filed on Feb. 11, 2013.

(51) Int. Cl.
| | | |
|---|---|---|
| C07C 309/00 | (2006.01) |
| C07C 209/00 | (2006.01) |
| C07C 211/63 | (2006.01) |
| C07C 213/02 | (2006.01) |
| C07D 233/58 | (2006.01) |
| C07D 295/037 | (2006.01) |
| C01B 17/45 | (2006.01) |

(52) U.S. Cl.
CPC ............ *C07C 209/00* (2013.01); *C01B 17/45* (2013.01); *C07C 211/63* (2013.01); *C07C 213/02* (2013.01); *C07D 233/58* (2013.01); *C07D 295/037* (2013.01)

(58) Field of Classification Search
None
See application file for complete search history.

(56) References Cited

U.S. PATENT DOCUMENTS

| 7,807,858 B2 | 10/2010 | Ishii et al. |
|---|---|---|
| 8,058,412 B2 | 11/2011 | Ishii et al. |
| 8,217,196 B2 | 7/2012 | Ishii et al. |
| 8,283,489 B2 | 10/2012 | Ishii et al. |
| 8,304,576 B2 | 11/2012 | Ishii et al. |
| 2008/0125589 A1 | 5/2008 | Ishii et al. |
| 2009/0250658 A1 | 10/2009 | Ishii et al. |
| 2010/0087673 A1 | 4/2010 | Ishii et al. |
| 2011/0201825 A1 | 8/2011 | Ishii et al. |
| 2012/0230906 A1 | 9/2012 | Johnson |
| 2012/0308881 A1 | 12/2012 | Tokuda et al. |

FOREIGN PATENT DOCUMENTS

| EP | 2243769 A1 | 10/2010 |
|---|---|---|
| EP | 2246322 A1 | 11/2010 |

OTHER PUBLICATIONS

International Searching Authority, USPTO, International Search Report and Written Opinion regarding corresponding PCT International Patent Application No. PCT/US2014/015859 issued May 16, 2014, pp. 1-12.

Li et al., "Synthesis and properties of triethylalkylammonium perfluorooctanesulfonates.(APFOS)" Journal of Fluorine Chemistry, Jul. 2004, vol. 125, Issue 7, pp. 1077-1080, [Retrieved from the Internet: <URL: http://www.sciencedirect.com]. p. 1077, col. 2, ln 3-11; p. 1078, col. 1, ln 3-4; p. 1078, col. 1, ln 20; p. 1079, col. 2, ln 6-14.

Barrera et al., "Perfluoroalkylsulfone reactions with nucleophiles" Journal of Fluorine Chemistry, Sep. 2002, vol. 117. Issue 1, pp. 13-16, [Retrieved from internet <URL: http://ac.els-cdn.com/S0022113902001707/1-s2.0-S0022113902001707-main.pdf>] p. 14, col. 1, ln 5.

Beyl, V., Niederprüm, H., Voss, P., Justus Liebigs Annalen der Chemie , 1970, 731, pp. 58-66.

Ahmed, M.G. et al., "Alkylations with methyl and ethyl fluorosulphonates", Chemical Communications, 1968, pp. 1533-1534.

Extended European Search Report issued in connection with corresponding European patent application No. EP14748620, Aug. 11, 2016, 10 pages.

International Bureau of WIPO, USPTO, International Preliminary Report on Patentability regarding corresponding PCT International Patent Application No. PCT/US2014/015859 issued Aug. 20, 2015, pp. 1-10.

*Primary Examiner* — Yong Chu
*Assistant Examiner* — Ana Z Muresan
(74) *Attorney, Agent, or Firm* — Duane Morris LLP

(57) ABSTRACT

The present invention is directed to methods for preparing a fluorosulfonate ester or a salt thereof, through a reaction of a dissolved sulfonyl fluoride ($R_FSO_2F$) with alkoxide anion ($RO^-$) optionally in the presence of an aprotic base (B), where $R_F$ is fluorine or a $C_1$-$C_8$ perfluoroalkyl group, and R is a primary alkyl or alkoxyalkyl. Alkoxide anion ($RO^-$) can be generated from a precursor such as an alcohol or silyl ester.

28 Claims, No Drawings

PREPARATION OF FLUOROSULFONATE ESTERS AND ONIUM SALTS DERIVED THEREFROM

CROSS-REFERENCE TO RELATED APPLICATIONS

The present application is a U.S. national phase application filed under 35 U.S.C. §371 of International Application No. PCT/US2014/015859, which was filed Feb. 11, 2014 and which claims priority to Provisional Patent Application No. 61/765,560 filed on Feb. 15, 2013 and Provisional Patent Application No. 61/763,087 filed on Feb. 11, 2013, each of which are incorporated herein by reference in their entirety.

BACKGROUND OF THE INVENTION

Field of the Invention

The present invention is directed to methods of producing fluorosulfonate esters, related salts, and related compositions comprising fluorosulfonate esters.

Background

Organic salts of fluorosulfonate ($FSO_3^-$) are useful, for example, as ion transport agents, in the fields of organic compound syntheses, as electrolytes and the like.

In 1968, the alkylation of triethylamine with ethyl fluorosulfonate in acetonitrile, to give tetraethylammonium fluorosulfonate, was reported (see Ahmed, M. G.; Alder, R. W.; James, G. H.; Sinnott, M. L.; Whiting, M. C., *Chemical Communications (London)* 1968, 1533-1534). The salt was not isolated, and no alcohol was present in the reaction.

In 2010, a quaternary ammonium fluorosulfonate was described by Ishii and coworkers (EP2243769, US20100087673) as a byproduct of the reaction of sulfuryl fluoride ($SO_2F_2$) with a hindered primary alcohol in the presence of triethylamine, giving the byproduct in 33% yield.

In 2012, a large number of organic fluorosulfonates were described in two patent applications (EP2535976 and US20120308881). Actual procedures for the preparation of organic fluorosulfonates were not reported, only possible methods. In particular, these applications included a general description of "a method in which a fluorosulfonic acid ester is reacted with a tertiary amine, a phosphine, or the like to obtain the fluorosulfonic acid salt through the quaternizing reaction of the tertiary amine or phosphine." Neither a description of methods of manufacture of the fluorosulfonate ester precursors, nor of the reaction of these esters with the amine, was given.

Some fluorosulfonate esters are highly toxic, especially the lower alkyl esters $MeOSO_2F$ and $EtOSO_2F$, making it impractical to handle these compounds on a commercially viable scale. It is preferable to generate a fluorosulfonate ester in the same pot as a substrate in order to minimize contact with and exposure to the fluorosulfonate ester.

Generation and reaction of fluorosulfonate esters in a single pot have been tried. However, a deoxyfluorination reaction, wherein an alcohol is converted to an alkyl fluoride, is generally reported. Organic fluorosulfonate salts, if present, are undesired byproducts obtained in low yield (see e.g., U.S. Pat. No. 7,807,858, U.S. Pat. No. 8,058,412, U.S. Pat. No. 8,217,196, U.S. Pat. No. 8,283,489, U.S. Pat. No. 8,304,576, US20080125589, US20090250658, US20100087673, US20110201825, EP2243769).

Perfluoroalkanesulfonate onium salts ($R_fSO_3^-M^+$), have been made from perfluoroalkanesulfonyl fluorides ($R_fSO_2F$), silyl ethers, and aprotic amines, in a single pot (see Beyl, V.; Niederprüm, H.; Voss, P., *Justus Liebigs Annalen der Chemie,* 1970, 731, 58-66); however, $SO_2F_2$ is not mentioned.

SUMMARY OF THE INVENTION

The present invention is directed to methods of producing fluorosulfonate esters or salts thereof by treatment of an alkoxide anion with sulfuryl fluoride in the presence of an aprotic base. The alkoxide anion is generated by, e.g., deprotonation of a parent alcohol or by fluoride ion cleavage of a silyl ether. The fluorosulfonate ester so produced may be isolated from the pot, or may react with more base or less-basic aprotic nucleophiles, either in situ or added afterward, to form an onium fluorosulfonate salt. If a stable fluorosulfonate ester is produced in the pot, protic amines may then be introduced and a number of products so obtained. Products of the invention are useful as electrolytes for electrochemical energy storage, and in other branches of industry.

Using the invention, unhindered primary alkoxides ($[RO^-]$) react with sulfuryl fluoride in the presence of an aprotic base (B), such as an aprotic amine, to form onium fluorosulfonates ($RB^+FSO_3^-$) in near quantitative yield.

As used herein "an aprotic base" such as "an aprotic amine" has no labile hydrogen atoms. For example, diethylamine is a protic amine and triethylamine is an aprotic amine. Other aprotic bases include carbonates, and fluorides as described herein. Examples of suitable carbonates include but are not limited to potassium carbonate, sodium carbonate, cesium carbonate, lithium carbonate and tetraethylammonium carbonate. Examples of suitable fluorides include but are not limited to alkali fluorides and organic onium fluorides. The alkoxide $[RO^-]$ is most simply generated by deprotonation of an alcohol ROH providing alkoxide anion $[RO^-]$, requiring an extra mole of B. Silyl ethers (e.g., ROSiMe3) may also be used as they react with the fluoride produced to generate $[RO^-]$ in a catalytic cycle. Both methods give yields of 90% or greater in most cases; the silyl ether method is preferred in that higher purity products are obtained from the pot. Silyl ethers are also suitable for polyalkylation of aprotic polyamines, and the production of stable fluorosulfonate esters in the pot.

Almost any aprotic amine with an aqueous pKa>4 may be used as the aprotic base. Primary, unhindered alkoxides react rapidly at −20° C. Hindered primary alkoxides react more slowly. Secondary alkoxides react rapidly but give lower yields of resulting fluorosulfonate ester or salt. For the production of an onium salt, the reaction is usually controlled by the rate of addition of $SO_2F_2$ into the pot and is preferably conducted below atmospheric pressure.

More broadly, the present invention is directed to a method for preparing a fluorosulfonate ester or a salt thereof, comprising: reacting a dissolved sulfonyl fluoride ($R_FSO_2F$) with an alkoxide anion ($RO^-$) generated in situ in the presence of an aprotic base (B), wherein $R_F$ is fluorine or a $C_1$-$C_8$ perfluoroalkyl group, and R is a primary alkyl or alkoxyalkyl group. When $R_F$ is fluorine, the sulfonyl fluoride is $SO_2F_2$. The alkoxide anion ($RO^-$) precursor can be a primary alcohol (ROH), or a silyl ether having a formula $ROSiR"_3$, $(RO)_2SiR"_2$, $(RO)_3SiR"$ or $(RO)_4Si$, wherein R is a primary alkyl or alkoxyalkyl group, and R" is an alkyl group such as methyl or ethyl.

In some embodiments, the aprotic base comprises a base selected from the group consisting of a tertiary amine ($R'_3N$), and a heteroaromatic tertiary amine (:NAr), wherein each R' is independently $C_1$-$C_6$ alkyl, alkoxyalkyl, cycloalkyl, morpholinyl, or bicycloalkyl, and :NAr is a nitrogen-containing heteroaromatic group. The resulting onium salt [RB$^+$] [R$_F$SO$_3^-$] can be a quaternary ammonium salt [R$_F$SO$_3$]$^-$[RR'$_3$N]$^+$, or a quaternary heteroaromatic salt [R$_F$SO$_3$]$^-$[RNAr]$^+$.

DETAILED DESCRIPTION OF THE INVENTION

The present invention is directed to a method for preparing a fluorosulfonate ester or a salt thereof, comprising: reacting a dissolved sulfonyl fluoride (R$_F$SO$_2$F) with an alkoxide anion (RO$^-$) generated in situ in the presence of an aprotic base (B), wherein R$_F$ is fluorine or a $C_1$-$C_8$ perfluoroalkyl group, and R is a suitable group such as a primary alkyl or alkoxyalkyl, which is optionally substituted by any other saturated or unsaturated alkyl group or an aryl group. References to "a primary alkyl or alkoxyalkyl" made in the present disclosure will be understood to encompass unsubstituted and substituted groups such as allyl, propargyl and benzyl (as described in the Examples). When R$_F$ is fluorine, the sulfonyl fluoride is SO$_2$F$_2$. The alkoxide anion (RO$^-$) can be generated in situ by from a primary alcohol (ROH), or a silyl ether.

Alkoxide from Alcohol:

In some embodiments, an alcohol is used to generate an alkoxide anion (RO$^-$) in a method for preparing a fluorosulfonate ester or a salt thereof. The method comprises reacting a dissolved sulfonyl fluoride (R$_F$SO$_2$F) with an alcohol (ROH) in the presence of an aprotic base (B) such as an aprotic amine, wherein R$_F$ is fluorine or a $C_1$-$C_8$ perfluoroalkyl group, and R is a primary alkyl or alkoxyalkyl as described herein. A fluorosulfonate ester or a resulting onium salt [RB$^+$] [R$_F$SO$_3^-$] can be isolated. For example, when the aprotic base comprises a tertiary amine (R'$_3$N), and the resulting onium salt is a quaternary ammonium salt [R$_F$SO$_3$]$^-$[RR'$_3$N]$^+$.

The reaction of ROH with dissolved SO$_2$F$_2$ is very slow, and [RO$^-$] must be generated in order for the reaction to commence. The relevant equations are given below:

$$ROH + B \rightleftharpoons RO^- + HB^+ \quad (1)$$

$$RO^- + SO_2F_2 \rightarrow ROSO_2F + F^- \quad (2)$$

$$ROSO_2F + B \rightarrow RB^+ + FSO_3^- \quad (3)$$

The alcohol ROH is rapidly and reversibly deprotonated by the base B to generate an alkoxide [RO$^-$](eq. 1) in low concentration, as the pKa of most primary alcohols (pKa=15-16) is well below the pKa of most aprotic amines (pKa=4-12). The alkoxide [RO$^-$] rapidly reacts with dissolved SO$_2$F$_2$ to form the fluorosulfonate ester ROSO$_2$F and fluoride (eq. 2). ROSO$_2$F is also present in low concentration as it reacts rapidly with B to form the onium salt RB$^+$FSO$_3^-$ (eq. 3).

For the production of onium salts, the buildup of either [RO$^-$] or ROSO$_2$F is undesirable as the following parasitic reaction may then take place:

$$RO^- + ROSO_2F \rightarrow ROR + FSO_3^- \quad (4)$$

In order to achieve high yields of onium salt, conditions which prevent the elevated concentration of either or both of [RO$^-$] or ROSO$_2$F must be employed, as the present invention discloses.

The prior art describes at length another parasitic reaction, namely, that of nucleophilic fluoride:

$$ROSO_2F + F^- \rightarrow RF + FSO_3^- \quad (5)$$

In the prior art, eq. (5) is optimized and eq. (3) is minimized. In the present invention, eq. (5) is minimized and eq. (3) is optimized.

Fluorosulfonate esters are also known to alkylate many weakly nucleophilic solvents such as ethers and nitriles (see Ahmed et al., *Chemical Communications* (*London*) 1968, 1533-1534). To minimize side reactions when using these solvents, low temperatures may be employed.

The alcohol (ROH) used in the present invention can be any suitable alcohol. For example, the alcohol can be a primary alcohol or alkoxyalcohol having from 1 to 20 carbon atoms. The alcohol can be a linear primary alcohol in some embodiments. R in the primary alkyl or alkoxyalkyl is optionally saturated or unsaturated and optionally substituted with other alkyl or aryl groups. Examples of suitable alcohols include but are not limited to methanol, ethanol, n-propanol, n-butanol, n-pentanol, n-hexanol, 2-methoxyethanol, 3-methoxypropanol, 2-ethoxyethanol, 3-ethoxypropanol, a higher poly(alkoxy)ethanol, allyl alcohol, propagyl alcohol, benzyl alcohol, a ring-substituted benzyl alcohol, 2-ethylhexanol and neopentanol. Any alcohol of the form R$_2$CHCH$_2$OH that doesn't have any reactive groups can be used. The alcohol (ROH) can be partially or wholly fluorinated, except for the hydroxyl carbon.

Amines which may be used include any aprotic amine with a pK>4. Examples of suitable amines include but are not limited to aprotic acyclic alkylamines, aprotic pyrrolidines, pyridines, piperidines, morpholines, azepines, N-alkylimidazoles, bicyclic aprotic amines such as 1,4-diazabicyclo[2.2.2]octane (DABCO), and a tricyclic aprotic amine such as hexamethylenetetramine. An aprotic acyclic alkylamine can be a tertiary amine such as trimethyl amine, triethyl amine, tripropyl amine, N,N-diethylmethyl amine, N,N-dimethylethyl amine. Pyridines and N-alkylimidazoles with a pKa>4 of the protonated base can be used, excepting certain hindered bases such as 2,6-di-tert-butylpyridine.

Some aprotic amines react more slowly than other aprotic amines, and some embodiments of the invention take advantage of this relative reactivity. For example, diisopropylethylamine ("DIPEA") is alkylated in some embodiments of the invention if present as the sole aprotic base. However, when DIPEA and trimethylamine are both present in the pot, trimethylamine is alkylated exclusively over DIPEA, and no evidence of alkylated DIPEA is found (see Example 15).

Alkoxide from Silyl Ether:

In some other embodiments, a silyl ether can be used to generate an alkoxide anion (RO$^-$) in a method for preparing a fluorosulfonate ester or a salt thereof. The method comprises reacting a dissolved sulfonyl fluoride (R$_F$SO$_2$F) with a silyl ether, optionally in the presence of an aprotic base (B) if an onium salt is the desired product, wherein R$_F$ is fluorine or a $C_1$-$C_8$ perfluoroalkyl group, and R is a primary alkyl or alkoxyalkyl. For example, the silyl ether can have a formula ROSiR"$_3$, (RO)$_2$SiR"$_2$, (RO)$_3$SiR" or (RO)$_4$Si, wherein R is a primary alkyl or alkoxyalkyl group, and R" is an alkyl group such as methyl and ethyl. R can be also the same as R". A resulting fluorosulfonate ester or an onium salt [RB$^+$] [R$_F$SO$_3^-$] can be isolated. For example, when the aprotic base comprises a tertiary amine (R'$_3$N), the resulting onium salt is a quaternary ammonium salt [R$_F$SO$_3$]$^-$[RR'$_3$N]$^+$. When R$_F$ is fluorine, the sulfonyl fluoride is SO$_2$F$_2$, and the resulting onium salt is a quaternary ammonium fluorosulfonate [FSO$_3$]$^-$[RR'$_3$N]$^+$.

Silyl ethers may be used to generate the alkoxide anion according to Equation (6):

$$ROSiR''_3 + F^- \rightarrow RO^- + FSiR''_3 \qquad (6)$$

Equation 6 proceeds readily at −20° C. in a suitable solvent such as acetonitrile. In some embodiments of the invention, a small amount of water can act as a fluoride source by reaction with $SO_2F_2$. In some embodiments of the invention, a small amount of the parent alcohol may be added as a fluoride source.

Silyl ethers are particularly useful for the production of stable fluorosulfonate esters. In order to achieve high yields of fluorosulfonate ester as a stable intermediate or isolated product, equations (3) and (4) must both be suppressed. Alkoxide [RO−] must react preferentially with $SO_2F_2$ and not with the product $ROSO_2F$. This is accomplished by creating conditions which maximize the concentration of $SO_2F_2$, minimize the concentration of [RO−](e.g., by slow addition of the [RO−] precursor to the pot), use of a less nucleophilic base B, and reduced temperature. More hindered alkoxide substrates give products with better stability than less hindered alkoxide substrates. If base B is a hindered aprotic amine (e.g., DIPEA) and the [RO−] precursor is a silyl ether, only small, substoichiometric amounts of B are required.

In some embodiments of the invention which use silyl ethers, ion pairs containing fluoride [F] can act as desilylating agents to generate [RO−] and produce stable fluorosulfonate esters without the use of any other aprotic base. In these embodiments of the invention, the aprotic base B is [F−](although technically [F−] acts as a desilylating agent and not as a base). In these embodiments of the invention, all reactants and solvent must be completely dry and free of residual alcohol. Suitable sources of fluoride, which are useful for the production of an onium salt and more particularly for the production of stable fluorosulfonate esters, include alkali fluorides such as potassium fluoride; cesium fluoride; mixtures of alkali fluorides or hydroxides (see Busch-Petersen, J.; Bo, Y.; Corey, E. J. *Tetrahedron Letters*, 1999, 40, 2065-2068); tetrabutylammonium fluoride (see Sun, H.; DiMagno, S. G. *Journal of the American Chemical Society,* 2005, 127, 2050-2051); tetramethylammonium fluoride and other tetraalkylammonium fluorides; phosphazenium fluorides (see Schwesinger, R.; Link, R.; Wenzl, P.; Kossek, S. *Chemistry—A European Journal* 2006, 12, 438-445); [S(NMe$_2$)$_3$]$^+$[Me$_3$SiF$_2$]$^-$ ("TASF", see Borrmann, T.; Lork, E.; Mews, R.; Stohrer, W.-D. *Journal of Fluorine Chemistry,* 2004, 125, 903-916) and other fluoride sources generally referred to in the literature as "naked" fluorides. More of these naked fluorides are outlined in Borrman et al., incorporated by reference herein in its entirety.

Silyl ethers which may be used include mono-, bis-, tris- and tetrakis-ethers, e.g., ROSiR''$_3$, (RO)$_2$SiR''$_2$, (RO)$_3$SiR'', and (RO)$_4$Si, where R can be a primary alkyl or alkoxyalkyl; and R'' can be an alkyl group. Monoethers (ROSiR''$_3$) are most reactive toward desilylation and are preferred. Examples of suitable silyl ethers include but are not limited to ROSiMe$_3$, (RO)$_2$SiMe$_2$, ROSiEt$_3$, and (RO)$_2$SiEt$_2$, and the like. Hereinafter the term ROSiMe3 is used as exemplary of all silyl ethers described under the invention. Volatile silyl ethers are preferred. R'' may be lower an alkyl group, preferably methyl or ethyl group.

Highly purified silyl ethers appear to react only slowly at −20° C., in contrast to the corresponding results at 22-50° C. observed when $SO_2F_2$ is replaced with perfluorobutanesulfonyl fluoride. see Beyl (paragraph 9).

The purity of silyl ethers used in the prior art with respect to free alcohol content was not specified. It also appears that there is no evidence of strong interactions between $SO_2F_2$ and, e.g., aprotic amines, so as to generate fluoride which sustains eq. 6. Nonetheless, less pure silyl ethers containing small amounts of alcohol can be used in some embodiments of the present invention. Residual [BH$^+$F$^-$] thus produced may be removed with NH$_3$ or a silylamine as described below.

Protic amines (e.g., diethylamine, etc) may also be used as pre-catalysts, to generate fluoride by reaction with $SO_2F_2$:

$$Et_2NH + SO_2F_2 + B \rightarrow Et_2NSO_2F + BH^+F^- \qquad (7)$$

Eq. (7) is very facile, even at −80° C., and the fluoride produced readily reacts via eq. (6). The byproducts (e.g., Et$_2$NSO$_2$F) are moderately reactive towards alcohols, alkoxides, and fluorosulfonate esters (see, e.g., King, J. F.; Lee, T. M.-L. *Canadian Journal of Chemistry,* 1981, 59, 362-372), and impurities arising from the introduction of a protic amine pre-catalyst can interfere with purification of an onium salt product.

The byproduct (e.g., FSiMe$_3$ b.p.=16° C.) is pumped off at the end of the reaction along with residual $SO_2F_2$.

The use of silyl ethers as [RO−] precursors for the production of onium salts offers significant advantages. The use of a silyl ether as an [RO−] precursor generally results in a clear and colorless pot liquor, in many cases without any solids present (other than added catalyst). When silyl ethers are used as reactants, often no solids are obtained at all, and the product is isolated in high purity. In comparison, when ROH is used as the [RO−] precursor, the subsequent ammonia quench gives significant amounts of ammonium fluoride, which must be filtered, and the crude product is often yellow in color. Onium salt products can also be ionic liquids, and recrystallization is then impractical. Silyl ethers are particularly useful for the production of ionic liquid onium fluorosulfonates having high purity.

Amines which may be used with silyl ethers include all of the amines described for use with alcohols, as well as tetramethylethylenediamine, N,N,N',N'-tetramethyl-1,3-diaminopropane, and other aprotic diamines and polyamines. Dicationic and polycationic fluorosulfonates may be produced by this method. Aprotic amines with reduced basicity (pKa<4) may also be added, and the temperature raised to a suitable level, to make onium salts which cannot be produced when an alcohol is used as the [RO−] precursor.

If a stable fluorosulfonate is produced as an intermediate, different protic bases may be added to the pot, and a range of products can be obtained.

Hindered Alkoxides and Secondary Alkoxides:

When secondary alkoxides are used, the yield is generally low. For example, as shown in Comparative Example 3, using isopropanol as a [RO−] precursor resulted in a 14% of yield of pure product. The yield is low because isopropyl fluorosulfonate tends to dissociate in polar media (Cafferata, L. F. R.; Desvard, O. E.; Sicre, J. E. *Journal of the Chemical Society, Perkin Transactions* 2 1981, 940-943).

In some embodiments, hindered primary alkoxides, particularly a partially fluorinated hindered alkoxide (e.g., R$_f$CH2OH), can be useful. As shown in Example 16, an isolable product FSO$_2$OCH$_2$CF$_3$ can be obtained.

Solvents which May be Used:

Any inert solvent capable of dissolving all of the reactants can be used; more polar solvents are preferred. Exemplary solvents include but are not limited to tetrahydrofuran (THF), ethyl ether, n-propyl ether, iso-propyl ether, 1,2-dimethoxyethane, methyl tert-butyl ether, acetonitrile, dichloromethane, 1,1,1-trichloroethane, chloroform, chlorobenzene, fluorobenzene, 1,2-difluorobenzene, toluene, di-n-butyl ether, and the like, and combinations thereof. Care must be taken to insure conditions which minimize byproducts from reaction with the solvent. Solvents known to react with $FSO_3R$ include THF and acetonitrile. Both are alkylated at measurable rates and can lead to byproducts. These side reactions are minimized by low temperatures. Ethyl ether, in addition to its relative inertness, is a suitable solvent for ethylations as the triethyloxonium cation has only one type of functional group, so byproducts are less likely. n-Propyl ether may be used for propylations. Similarly, as described in the prior art (Wong, C.-P.; Jackman, L. M.; Portman, R. G. *Tetrahedron Letters*, 1974, 15, 921-924), phosphate esters $(RO)_3P=O$ may be used as solvent for onium salt production, wherein the (RO) of $(RO)_3P=O$ has the same R group as the [RO⁻] precursor. Many aprotic polar solvents, such as dimethylformamide (DMF), dimethyl sulfoxide (DMSO), 1,3-dimethyl-3,4,5,6-tetrahydro-2(1H)-pyrimidinone (DMPU), hexamethylphosphoramide (DMPU), are too reactive with fluorosulfonate esters to be of use (see Wong).

Liquid neat bases may be used without any solvent. If the resulting product is an ionic liquid, it may be used as a solvent or cosolvent.

Method, Order, and Rate of Addition of the Reactants:

Generally, $SO_2F_2$ is infused into the head space above, or injected into, a stirred solution of the [RO⁻] precursor and the base (B). For the production of stable fluorosulfonate esters, a silyl ether may be added to a mixture of B and $SO_2F_2$. Alternatively, B may be added to a mixture of an [RO⁻] precursor and $SO_2F_2$. Side reactions are minimized by keeping the concentration of [RO⁻] low, the temperature low, and for onium salt production, a high concentration of B. Thus in one embodiment of the invention, an [RO⁻] precursor is slowly added to a solution of B and $SO_2F_2$. In another embodiment, both $SO_2F_2$ and an [RO⁻] precursor are slowly added simultaneously to a solution of B. For $SO_2F_2$ gas and an amine such as $Me_3N$ or $Et_3N$, excellent yields have been obtained by infusing $SO_2F_2$ into the head space over an [RO⁻] precursor/B solution under full static vacuum at −15 to −17° C., and increasing the pressure until the heat of reaction matches the cooling power.

The fluorosulfonate ester so produced may be isolated from the pot (if sufficiently stable), or may react with more B to form an onium fluorosulfonate salt. If a stable fluorosulfonate ester is produced in the pot, protic amines may then be added and a number of products so obtained. In some embodiments of the invention, the pot contents are transferred to a second pot containing an excess of protic amine. In some embodiments, the fluorosulfonate ester is a stable ester, and is treated with a protic amine; and a resulting product is a neutral protic or aprotic amine. The stable fluorosulfonate ester can be also treated with a protic amine; and a resulting product is an onium salt.

The reaction of a dissolved sulfonyl fluoride $R_FSO_2F$ with a silyl ether $ROSiMe_3$ in the presence of fluoride can result in a stable solution of $R_FSO_2R$. The stable solution is mixed with a protic substrate (HZ), producing an alkylated or polyalkylated substrate $R_nZ$, wherein the R of $R_nZ$ comes from the silyl ether $ROSiMe_3$, and n is an integer from 1 to 100,000. The substrate HZ is chosen from ammonia, a primary amine, a secondary amine, or a polymer containing one or more amines of any degree of substitution, and the product is a primary amine, a secondary amine, a tertiary amine, a tetraalkylammonium salt, a spiroammonium salt (e.g., $[N(CH_2)_4)_2]^+[FSO3]^-$ and the like), a combination thereof, or an alkylated polymer thereof. A relatively hindered aprotic base (e.g., DIPEA and the like) may be added to the pot at suitably low temperatures to absorb the protons resulting from addition of protic amines to stable solutions of fluorosulfonate esters.

Molar Ratio of Reactants:

When an alcohol (ROH) is used as an [RO⁻] precursor, best results are obtained when ROH is the limiting reagent and is completely consumed. This is especially true of the higher boiling alcohols. To drive the reaction to completion, the molar ratio of the aprotic base to the alcohol (B:ROH) is preferably 2:1 or greater. For example, good results have been obtained by using a ratio of 2.5:1. The molar ratio of the sulfonyl fluoride ($R_FSO_2F$ such as $SO_2F_2$) to alcohol ($SO_2F_2$:ROH) is 1:1 or greater, for example, slightly greater than 1:1.

Best results are obtained when the reactants and solvent are dry. Water consumes 1 mole of $SO_2F_2$ and two moles of B per mole of water, so damp reactants will require greater amounts of both $SO_2F_2$ and B. Furthermore, the products are all water- and alcohol-sensitive, and HF can be generated during the drying process if the product contains any moisture or residual alcohol. In some embodiments of the invention, e.g. when silyl ethers are used as reactants and B is an aprotic amine, addition of small amounts of water to the nascent pot (i.e., after cooling and saturating with $SO_2F_2$) can initiate the process, by reaction with $SO_2F_2$ to generate fluoride [F⁻] in situ.

When a silyl ether is used as a reactant, it may be used in excess relative to B, or not used in excess, depending on which reagent is more expensive, for example.

Concentrations of reactants can range from 0.001 to >10 molal. Molalities generally go down as the molecular weight of the reactants increases. For example, for the system $MeOH/Me3N/SO_2F_2$ (see Example 1), 1.9 molal methanol in acetonitrile (−15° C.) was used, and a 79% yield was obtained. For the system $EtOH/Et_3N/SO_2F_2$ (see Example 2), 0.8 molal ethanol in acetonitrile (−17° C.) was used, and a 96% yield was obtained.

Pressure:

Operating pressure ranges from full static vacuum to well above atmospheric pressure. Operating pressure is below atmospheric pressure in some embodiments. The reaction may be conducted at superatmospheric pressures, but the advantage of speed can be offset by the safety hazard. If highly reactive lower fluorosulfonate esters are used as intermediates, limitations with the cooling power of the pot also become more important at higher pressures. However, if production of the fluorosulfonate ester as a stable intermediate (or isolated product) is desired, superatmospheric pressures can be useful. The observations made using pressure-gated addition of $SO_2F_2$ indicate that the pressure of $SO_2F_2$ needed to maintain a given rate of reaction appears to increase as the reaction temperature is lowered, and as the reaction progresses. There is no limiting low addition pressure for the $SO_2F_2$, only an increase in addition time as the pressure is reduced. The lowest absolute pressure which may be employed approaches the static vapor pressure of the pot. Practically, in some experiments, a pressure used is in the range of from 50 Torr (beginning) to 400 Torr (end), at −17° C., when ROH is used as the [RO⁻] precursor.

Temperature:

The reaction of acetonitrile solutions of $SO_2F_2$ with an [RO⁻] precursor in the presence of B is generally facile at −20° C., whereas without B, reaction occurs only slowly or not at all. Higher temperatures may also be employed without departing from the invention. In some embodiments of the invention, temperatures during the course of the reaction can range as high as 60° C. or greater, for example, when less reactive or hindered fluorosulfonate esters are intermediates, and an onium salt is the product. Lower temperatures can also be employed, down to the freezing point of the solvent system.

Quench:

Quenching is optional and can be performed using ammonia. The addition is exothermic. Ammonia addition serves two main purposes: most [BH$^+$F$^-$] salts, if present, are converted to insoluble ammonium fluoride; and residual sulfonyl esters, if any, are eliminated from the pot. Other quenching agents may be used if ammonia reacts with the product or solvent. For most aprotic amines, [BH$^+$F$^-$] is completely eliminated from dichloromethane by treatment with ammonia. When acetonitrile is used, [BH$^+$F$^-$] is less completely eliminated by treatment with ammonia; lower temperatures are helpful in this regard. Ammonium fluorosulfonate is also poorly soluble in most aprotic solvents and if any [BH$^+$][FSO3$^-$] is present, it may similarly be removed from the crude pot by treatment with ammonia. An exception is the salt [DIPEA-H$^+$] [FSO3$^-$] (see Example 15) which is not readily deprotonated by ammonia, and stronger bases or a large ammonia excess must be used for this contaminant.

Treatment with Silylamines:

The aliphatic alkylammonium fluorosulfonate products of the invention are all hygroscopic, and fluorosulfonate is water-sensitive. Elimination of water and residual alcohol from the crude product is therefore important. The clear pot contents obtained directly or via filtration may be effectively dehydrated and scrubbed free of fluoride by treatment with a silylamine. The crude product may also be similarly treated within the invention. The crude product may be treated with silylamine in the absence or presence of solvent. The amount of silylamine needed should be sufficient to react with any water, fluoride, and intermediate silanols present in the pot. Excess silylamine, along with other products (amines, ROSiMe3, and Me$_3$SiOSiMe$_3$), are removed under reduced pressure and/or elevated temperature, and a more pure product obtained. Silyamines which may be used include but are not limited to hexamethyldisilazane, dimethylaminotrimethylsilane, diethylaminotrimethylsilane, and the like, and combinations thereof. Lower boiling silylamines are preferred. For higher-boiling alcohol or ether contaminants not easily evacuated, purification after treatment may also include a wash or co-distillation using a solvent which dissolves ROSiMe$_3$ without dissolving the product. The choice of a proper solvent depends on the product being purified. Generally, alkyl ethers and hydrocarbons are suitable as most of the onium products of the invention are poorly soluble in these solvents.

Toxicity of Reactants:

SO$_2$F$_2$ is a highly toxic and completely odorless and colorless gas. Thus, significant precaution must be used. All reactions should be conducted in areas having sufficient ventilation. On the lab scale, this means all reactions must be conducted inside a fume hood at least until the quench gas (NH$_3$) is removed. On the industrial scale, proper ventilation should be designed and proper safety measures followed. Although SO$_2$F$_2$ is toxic, it is a gas, and when contained or ventilated is much less hazardous to work with than, e.g., FSO$_3$Me, a liquid.

The invention makes it possible to prepare, optionally isolate, and use powerful alkylating agents in a safe manner on a large scale for low cost. The invention obviates the need for the use of corrosive sulfonic acids, or manipulation of severely toxic FSO$_3$R esters (e.g., methyl and ethyl fluorosulfonate) outside of the reactor. Many fluorosulfonate esters are heat sensitive as well, and isolation of such esters through, e.g., distillation can be impractical. Sulfuryl fluoride is inexpensive and widely used as a fumigant. The invention eliminates higher halogens (chloride, bromide, iodide) from the process stream. Higher halogens are a perennial contaminant of quaternary ammonium salts and especially interfere with the operation of lithium ion batteries, for example. FSO$_3$R esters are more reactive than alkyl chlorides or sulfates, and are inexpensive to prepare with this invention. Alkyl chlorides, bromides, sulfates, tosylates, mesylates, and triflates can be replaced in many instances with the less-costly products of this invention.

For the purpose of illustration, tertiary amine (R'$_3$N) is used as the aprotic base. However, the aprotic base is not limited to tertiary amine only. In some embodiments, the aprotic base comprises an alkali carbonate, an alkaline earth carbonate, or quaternary ammonium carbonate, fluoride, or a base such as a heteroaromatic tertiary amine (:NAr), wherein each R' is independently a C$_1$-C$_6$ alkyl or alkoxyalkyl, a cycloalkyl, morpholinyl, or bicycloalkyl, and :NAr is a nitrogen-containing heteroaryl group. The resulting onium salt [RB$^+$] [R$_F$SO$_3^-$] can be a quaternary ammonium salt [R$_F$SO$_3$]$^-$[RR'$_3$N]$^+$ or a quaternary heteroaromatic salt [R$_F$SO$_3$]$^-$[RNAr]. The R of the resulting onium salt comes from the [RO$^-$] precursor. The R' comes from the corresponding aprotic base.

Compositions Comprising the Products:

The present invention is further directed to compositions comprising the products. In some embodiments, a composition comprises a product of the present invention (i.e., [FSO$_3$]$^-$[RR'$_3$N]$^+$, wherein R is a primary alkyl or alkoxyalkyl; each R' is independently an alkyl, N,N-cycloalkyl, or alkoxyalkyl, tetrakis ammonium salts thereof, aromatic heterocyclic quaternary ammonium salts thereof, having a purity of 95% or greater, 98% or greater, 99% or greater, 99.5% or greater, 99.9% or greater, 99.999% or greater.

The present invention is also directed to articles of manufacture, compositions, and/or devices comprising the products of the processes described herein. For example, the ionic products of the invention can be used as electrolytes in energy storage devices, batteries, supercapacitors (e.g., electrochemical double-layer capacitors), and the like. The non-ionic alkylated products of the invention are widely used in many branches of industry.

EXAMPLES

Example 1

Tetramethylammonium Fluorosulfonate. A sealed 2-liter pressure reactor (Parr Instrument Company) was charged with acetonitrile (781 grams), methanol (48 grams, 1.5 mole) and trimethylamine (283 grams, 4.8 moles). The reactor was cooled to −20° C. and evacuated to constant static pressure with stirring. Sulfuryl fluoride (155.3 grams, 1.52 moles) was added with stirring under reduced pressure over 140 minutes at a temperature of −15° C., then stirred for 4 hours below −15° C. The reactor was pressurized with ammonia through a dip tube to a pressure above atmospheric. After stirring for 5 minutes the reactor was vented and opened. The reactor contents were filtered and the clear colorless filtrate was separated from the copious white solid precipitate. The filtrate was concentrated to dryness on a rotary evaporator, giving 10.6 grams of solid. The dried solids were combined and recrystallized from 1 Kg water to give pure tetramethylammonium fluorosulfonate (206 grams, 1.18 mole, 78.9%), mp=342-345° C. with decomposition. APCI MS m/e 74 (M+), 247 (2M+/FSO3−).

Example 2

Tetraethylammonium Fluorosulfonate. A sealed 2-liter Parr reactor was charged with acetonitrile (784 grams), ethanol (28.2 grams, 0.61 mole) and triethylamine (211 grams, 2.1 moles). The reactor was cooled to −19° C. and evacuated (12 Torr). Sulfuryl fluoride (63.5 grams, 0.62 moles) was added with stirring under reduced pressure over 68 minutes at a temperature of −17° C., then stirred for 35 minutes below −17° C. The reactor was pressurized with ammonia through a dip tube to about 600 Torr; the temperature rose from −20 to +3° C. After stirring for 10 minutes the reactor was opened. The reactor contents were filtered and the clear colorless filtrate was separated from the white solid precipitate. The filtrate was concentrated to dryness (90° C./0.8 Torr) on a rotary evaporator, giving 135 grams of product (0.59 moles, 96% from EtOH) as a white solid. The product was recrystallized from one-third its weight of water and dried in a vacuum oven (60° C.) to give a pure crystalline solid in two crops, mp=296-298° C. with decomposition. The product $Et_4NFSO_3$ is soluble in dichloromethane (0.5 M @ 25° C.). APCI MS m/e 130 (M+), 359 (2M+/FSO3−).

Example 3

N-Hexyl-N-methylpyrrolidinium Fluorosulfonate. A sealed 2-liter Parr reactor was charged with acetonitrile (779 grams), n-hexanol (50 grams, 0.49 mole) and N-methylpyrrolidinone (127.7 g, 1.5 mole). The reactor was evacuated to a static pressure of 76 Torr @15° C. Sulfuryl fluoride (49.4 grams, 0.48 moles) was added with stirring to the stirred solution over 74 minutes and the temperature maintained at 15-17° C. The reactor was warmed to 26° C. and stirred an additional two hours. Excess ammonia gas was introduced, followed by sparging of the reactor with nitrogen gas through a dip tube. The reactor was opened, the contents filtered, and the clear filtrate rotovapped to give a residue (159 g) with an odor of hexanol. This residue was heated to 130° C. until a pressure of 1.1 Torr was reached, then cooled to give a clear golden glassy solid (113.1 g, 0.42 mole, 86%), mp=123-125° C.

Comparative Example 1

A 2 liter Parr reactor was charged with acetonitrile (630 grams), dimethyl sulfide (22.4 grams, 0.36 mole), N,N-diisopropylethylamine ("DIPEA"), 130 g, 1 mole), and methanol (12.8 g, 0.4 mole), cooled to −5° C., and evacuated (44 Torr). $SO_2F_2$ (46.6 grams, 0.45 mole) was added with stirring at 700 Torr over a period of 13 minutes, the temperature rising from −5 to +9° C. The reactor contents were cooled to 0° C. over an hour, then allowed to warm up overnight (9 hours). The pressure at the end was 210 Torr @ 12° C. The reactor was evacuated and ammonia (9.1 g, 0.53 mole) added. After 20 minutes the reactor was opened and the solid filtered off. The clear filtrate was concentrated to a solid, washed with ethanol (100 g), and dried in a vacuum oven at 45° C. Sublimate was observed on the walls of the vacuum oven after a few hours. The remaining solid (65.4 g) was found to be N-ethyl-N-methyl-N,N-diisopropylammonium fluorosulfonate by mass spectroscopy (APCI MS m/e=144), 0.27 moles, 67%.

Example 4

1-Propyl-3-methylimidazolium Fluorosulfonate. A 2 liter Parr reactor was charged with acetonitrile (750 g), N-methylimidazole (250 g, 3.04 mole) and n-propanol (60 g, 1 mole), cooled to −20° C., and evacuated. $SO_2F_2$ was introduced over 77 minutes at a temperature of −17 to −20° C. at a gated pressure of 500 Torr. The reactor was stirred for 17 hours at −17 to −10° C. and the pressure dropped to 27 Torr during this time. The reactor was evacuated, 22.6 g ammonia introduced, and the reactor warmed to +10° C. The contents were filtered and the cake washed with acetonitrile (2×100 mL). The clear colorless filtrate was rotovapped (48° C./8 Torr) to an oil. N-methylimidazole was then distilled off in a 100° C. oil bath at 0.3 Torr; 155 g recovered. The colorless crystalline residue consisted of the product (222.9 g, 0.99 mole, 98%), mp≈26° C. A further attempt at removal of traces of imidazole in a 118° C. bath at 6 microns vacuum removed an additional 4.5 g imidazole and imparted a yellow color to the residue, the entire mass melting at 23.6-25.1° C. Yield, 97%. APCI MS m/e 125 (M+), 349 (2M+/FSO3−).

Example 5

N-Ethylpyridinium Fluorosulfonate. A 2 liter Parr reactor was charged with acetonitrile (856 g), ethanol (46.1 g, 1 mole, and pyridine (236.2 g, 3 mole), cooled to −20° C., and evacuated (10 Torr). $SO_2F_2$ was added with stirring over 27 minutes at a temperature of −19 to −20° C. at a gated pressure of 500-700 Torr. The contents were stirred for 23 hours with stepwise increases in temperature to −3° C., maintaining at all times subatmospheric pressure. The endpoint pressure was 163 Torr. The reactor was evacuated and ammonia (26 g, 1.5 mole) introduced. The contents were then filtered and the clear colorless filtrate rotovapped at 58° C./4 Torr. The resulting oil was further heated in a 50-60° C. water bath to a vacuum of 10 microns, yielding a colorless solid (174.6 g, 0.84 mole, 84%), the entire mass melting at 49.8-52.0° C. APCI MS m/e 108 (M+), 315 (2M+/FSO3−).

Example 6

Tetraethylammonium Fluorosulfonate. A 2 liter Parr reactor was charged with acetonitrile (461 g), ethoxytrimethylsilane (78.7 g, 0.66 mole), and triethylamine (81.3 g, 0.804 mole), cooled to −20° C., and evacuated (13 Torr). $SO_2F_2$ (64.7 g, 0.63 mole) was added with stirring over 103 minutes at a gated pressure of 300-500 Torr. The contents were stirred overnight at −14° C. and the pressure dropped to 75 Torr. The reactor was evacuated, warmed to 27° C., and brought to atmospheric pressure with nitrogen gas. The contents, a clear, light yellow liquid, were rotovapped to near dryness (55° C./6 Torr). The resulting slightly damp solid was stirred with toluene (500 mL) and dichloromethane (25 mL) at 80° C. until a homogenous suspension was achieved (90 minutes). The suspension was filtered. A white solid and a light yellow filtrate were observed. The solid was dried in a vacuum oven at 80° C., giving the product (141.7 g, 0.62 mole, 97.5%), m.p.=301-302° C. with decomposition.

Example 7

Allyltriethylammonium Fluorosulfonate. A 2 liter Parr reactor was charged with acetonitrile (624 g), triethylamine (111 g, 1.1 mole) and allyl alcohol (28.95 g, 0.5 mole), cooled to −19° C. and evacuated (9 Torr). SO$_2$F$_2$ (51.7 g, 0.51 mole) was added with stirring over 2 hours at −17° C. with a gated pressure of 139 Torr. After an additional 2 hours at −17 to −18° C., the reactor pressure dropped to 20 Torr. Ammonia (11.2 g, 0.66 mole) was introduced, the reactor warmed to 23° C., and the contents filtered. The clear colorless filtrate was rotovapped (46° C./5 Torr) to dryness. The crude solid was recrystallized from dichloromethane/toluene and dried overnight in a vacuum oven at 45° C., giving the product (118.7 g, 0.49 mole, 98%), m.p.=212-219° C. APCI MS m/e 142 (M$^+$), 383 (2M$^+$/FSO3$^-$).

Example 8

N-Ethyl-N-methylpyrrolidinium Fluorosulfonate. A 2 liter Parr reactor was charged with acetonitrile (668 g), ethoxytrimethylsilane (60 g, 0.51 mole) and N-methylpyrrolidine (42.3 g, 0.5 mole). The reactor was cooled to −19° C. and evacuated (14 Torr). SO$_2$F$_2$ was added with stirring over 37 minutes at −19° C. with a gated pressure of 100-400 Torr. The reactor was stirred overnight and the pressure dropped to 53 Torr. The reactor was evacuated and 2.3 g ammonia added. The reactor was warmed to 28° C., infilled with nitrogen, and the contents, a slightly turbid colorless liquid, were polish filtered and the filtrate rotovapped (45° C./5 Torr) and dried at <1 Torr to give 102.3 g of a white solid (0.48 mole, 97%) as a highly deliquescent solid not easily recrystallizable, mp=123-157° C. APCI MS m/e 114 (M$^+$).

Example 9

Propargyltriethylammonium Fluorosulfonate. A 2 liter Parr reactor was charged with acetonitrile (638 g), propargyl alcohol (28.6 g, 0.51 mole) and triethylamine (113.7 g, 1.12 mole), cooled to −26° C., and evacuated (7 Torr). SO$_2$F$_2$ was added with stirring over 116 minutes at a gated pressure of 50-75 Torr. After 23 more minutes at −25° C. the pressure had dropped to 17 Torr. The reactor was evacuated and ammonia (19 g, 1.1 mole) added. The reactor was then warmed to +12° C., infilled with nitrogen, and the clear colorless contents rotovapped and dried at 1 Torr overnight to give the product (118.5 g, 0.495 mole, 97%) as nearly colorless crystals, mp=160-164° C. Recrystallization from acetonitrile/toluene gave 98 grams, mp=163-169° C. APCI MS m/e 140 (M$^+$), 379 (2M$^+$/FSO3$^-$). The product is not hygroscopic.

Example 10 n-Propyltrimethylammonium Fluorosulfonate. A 2 liter Parr reactor was charged with acetonitrile (1062 g), propoxytrimethylsilane (211.6 g, 1.6 mole), and trimethylamine (90.5 g, 1.53 mole), cooled (−19° C.), and evacuated (96 Torr). During the evacuation 15.8 grams trimethylamine was removed and captured by an ion exchange resin trap, leaving 74.7 g (1.26 mol) in the pot. SO$_2$F$_2$ (130.1 g, 1.27 mole) was added with stirring over 217 minutes at −9 to −12° C. with a gated pressure of 400 Torr, and stirred at −12° C. for 12 hours. The pressure dropped to 132 Torr. The reactor was warmed to 0° C. and evacuated (68 Torr), then opened. The clear, colorless liquid was rotovapped (45° C./1.8 Torr) to give a white solid (264 g), which was recrystallized on a rotary evaporator (0-13° C./60-20 Torr) from dichloromethane/toluene/hexamethyldisilazane (1200 mL/300 mL/25 g) and dried (45° C./1 Torr) to give the product (250 g, 1.24 mole, 99%) as fine waxy flakes, mp=98-99.5° C. APCI MS m/e 102 (M$^+$), 303 (2M$^+$/FSO3$^-$).

Example 11

Ethyltrimethylammonium Fluorosulfonate. A 2 liter Parr reactor was charged with acetonitrile (811 g) and ethoxytrimethylsilane (120.8 g, 1.02 mole), cooled (−21° C.), and evacuated (11 Torr). Trimethylamine (59.5 g, 1.01 mole) was added and the pressure rose to 64 Torr at −20° C. SO$_2$F$_2$ (103.8 g, 1.02 mole) was added with stirring over 79 minutes at −9 to −15° C. with a gated pressure of 300 Torr. The reactor was stirred for 12 hours at −10° C., warmed to 0° C., evacuated, and infilled with nitrogen. The contents were filtered through a fine fritted glass filter and the clear colorless filtrate rotovapped (45° C./80 Torr) to dryness and the resulting solid dried (45° C./1 Torr) overnight to give the product (182.2 g, 0.97 mole, 96%), m.p.=278-286° C. with decomposition. Recrystallization from acetonitrile/toluene gave a product with m.p.=292-295° C. (d). APCI MS m/e 88 (M$^+$), 275 (2M$^+$/FSO3$^-$).

Comparative Example 2

Neopentanol/Et3N/SO$_2$F$_2$: A 2 liter Parr reactor was charged with acetonitrile (924 g), neopentanol (103 g, 1.16 mole) and triethylamine (260 g, 2.57 mole), cooled (−17° C.) and evacuated (14 Torr). SO$_2$F$_2$ (120.6 g, 1.18 mole) was added with stirring over 70 minutes at −9° C. with a gated pressure of 300 Torr. The reactor was stirred overnight (15 hours) at −11° C. and the pressure dropped to 30 Torr. The reactor was warmed to 0° C., evacuated (29 Torr), and ammonia (25.3 g, 1.5 mole) added. The reactor was infilled with nitrogen and opened, revealing a heavy suspension. This was filtered off and the clear, colorless filtrate rotovapped (45° C./80 Torr), leaving a residual liquid which fumed mildly. The liquid was distilled in a 47° C. bath giving a clear colorless distillate (93 g), bp=29° C./6 Torr. This was redistilled in a 60° C. bath, bp 41° C./14 Torr, giving 81 g of a slightly cloudy distillate. This distillate was subjected to FTIR analysis and no peaks above 3000 cm$^{-1}$ were found. The flask was lightly stoppered and set aside. After a day, the contents erupted, blowing out the stopper, and left a dark red oily residue in the flask and fume hood. The residue was not further analyzed.

Comparative Example 3

Isopropyltriethylammonium Fluorosulfonate. A 2 liter Parr reactor was charged with acetonitrile (862 g), isopropanol (60.1 g, 1 mole) and triethylamine (250 g, 2.47 mole), cooled (−20° C.) and evacuated (12 Torr). SO$_2$F$_2$ (107.2 g, 1.05 mole) was added with stirring over 160 minutes at −19° C., with a gated pressure of 50-400 Torr. The reactor was stirred an additional 45 minutes and the pressure dropped from 369 Torr to 321 Torr. The reactor was then evacuated (33 Torr), warmed to −10° C., and ammonia (22.7 g, 1.3 mole) added. The reactor was then warmed to +20° C., infilled with nitrogen, and the contents filtered. The filtrate, a clear, slightly colored liquid, was rotovapped (45° C./32 Torr) giving an oily residue (180 g). The residue was taken up in dichloromethane (500 mL) and sparged with ammonia, giving precipitated NH$_4$F which was filtered off. The oil was taken up in dichloromethane (500 mL) and hexamethyldisilazane (7 g) and rotovapped (200 Torr) until solids began to appear. The flask was then transferred to a bed of dry ice "rice" until well chilled, then immediately filtered, giving 23.9 g of crude solid. Two more crops were obtained in this fashion by concentration of the filtrate for a total of 61 grams crude solid. The crude solid was recrystallized from dichloromethane/toluene to give the pure product (35.1 g, 0.14 mole, 14%), mp=278-280° C. with decomposition. APCI MS m/e 144 (M$^+$), 387 (2M$^+$/FSO3$^-$).

Example 12

Benzyltriethyammonium Fluorosulfonate. A 2 liter Parr reactor was charged with acetonitrile (864 g), benzyl alcohol (117.5 g, 1.1 mole) and triethylamine (244 g, 2.41 mole), cooled (−22° C.) and evacuated (10 Torr). SO$_2$F$_2$ (113.8 g, 1.15 mole) was added with stirring over 120 minutes at −18 to −20° C. with a gated pressure of 100 Torr. The reactor was stirred for 18 minutes at −20° C. and the pressure dropped to 54 Torr. The reactor was evacuated, ammonia (20.1 g, 1.18 mole) added, and the reactor stirred overnight while warming to room temperature. The reactor was infilled with nitrogen, opened, and the contents filtered. To the clear colorless filtrate was added hexamethyldislazane (32 g) and toluene (750 mL) causing a precipitate, which redissolved upon warming on a rotary evaporator. The clear solution was rotovapped (38° C./77 Torr) to about 700 mL and a precipitate evolved. The flask was then rotated on ice and filtered. The cake was compressed with a rubber dam and rinsed with toluene (50 mL). The cake was dried at 45° C./1 Torr to give the product as a white solid (247.4 g, 0.85 mole, 77%), mp=137-139° C. A second crop was obtained from the filtrate as a light yellow solid (39.5 g, 0.135 mole, 12%), mp=124-138° C. APCI MS m/e 192 (M$^+$), 483 (2M$^+$/FSO3$^-$).

Example 13

(2-Methoxyethyl)trimethylammonium Fluorosulfonate. A 2 liter Parr reactor was charged with acetonitrile (842 g) and (2-methoxyethoxy)trimethylsilane (192.4 g, 1.29 mole), cooled (−17° C.), and evacuated (9 Torr). Trimethylamine (75.2 g, 1.27 mole) was added and the pressure rose to 78 Torr at −19° C. SO$_2$F$_2$ (132.8 g, 1.3 mole) was added with stirring over 134 minutes at −15 to −17° C. with a gated pressure of 125-250 Torr. The reactor was then stirred for 4 hours at −15 to −17° C. and the pressure dropped to 116 Torr. The reactor was evacuated and warmed to −2° C., infilled with nitrogen, and opened. The contents, a clear, colorless liquid, were rotovapped dry and further rotated (45° C./2.2 Torr) for four hours to give the product as a white solid (271.8 g, 1.25 mole, 98.5%), mp=93° C. APCI MS m/e 118 (M$^+$), 335 (2M$^+$/FSO$_3^-$).

Example 14

(2-Ethylhexyl)(triethyl)ammonium Fluorosulfonate. A 2 liter Parr reactor was charged with acetonitrile (653 g), 2-ethylhexanol (97.5 g, 0.75 mole) and triethylamine (174 g, 1.71 mole), cooled to −19° C., and evacuated (12 Torr). SO$_2$F$_2$ (78 g, 0.76 mole) was added with stirring over 173 minutes at −15 to −21° C. with a gated pressure of 200 Torr. The reactor was stirred for 12 hours at −21° C. and the pressure dropped to 48 Torr. The reactor was warmed to −10° C. and evacuated (22 Torr). Ammonia (17.6 g, 1 mole) was added over 15 minutes and the reactor then warmed to +19° C., infilled with nitrogen, and opened. Solid NH$_4$F (26 g, 0.7 mole) was filtered off and the clear light yellow filtrate rotovapped (45° C./1.4 Torr) to give 207 grams of a viscous yellow oil with a faint odor of octanol. The oil was stirred at 45° C. in a 36 micron vacuum for 17 hours to give the product (200 g, 0.64 mole, 85%) as an odorless light yellow oil. APCI MS m/e 214 (M$^+$), 527 (2M$^+$/FSO3$^-$).

Example 15

A 2 liter Parr reactor was charged with acetonitrile (936 g), ethanol (39.8 g, 0.86 mole), DIPEA (249 g, 1.9 mole) and trimethylamine (56.7 g, 0.96 mole), cooled to −35° C., and evacuated (6 Torr). SO$_2$F$_2$ (87 g, 0.85 mole) was added with stirring over 46 minutes at −30 to −38° C. with a gated pressure of 100-150 Torr. The reactor was stirred for 90 minutes at −25° C. and the pressure dropped to 11 Torr. Ammonia (28.6 g, 1.7 mole) was added over 7 minutes and the reactor then warmed to +12° C., infilled with nitrogen, and opened. The white solid was filtered off and the filtrate rotovapped (65° C./9.7 Torr) to give 147 g of a white solid. APCI mass spectroscopy of this solid showed it to be a mixture of ethyltrimethylammonium fluorosulfonate (m/e 88) and DIPEA-H$^+$ fluorosulfonate (m/e 130). No peak at m/e 158 was found, indicating that DIPEA was not alkylated in this reaction.

Example 16

2,2,2-Trifluoroethyl fluorosulfonate (unoptimized procedure). A 2 liter Parr reactor was charged with dichloromethane (1.3 Kg) and DIPEA (133 g, 1.03 mole), cooled to −20° C., and evacuated (48 Torr). Sulfuryl fluoride (102.3 g, 1 mole) was added with stirring over 1 hour at −19° C. with a gated pressure of 100-200 Torr. The reactor was stirred an additional 18 hours at −21° C. and the pressure dropped to 72 Torr. The reactor was evacuated (47 Torr), warmed to 25° C., infilled with nitrogen, and opened. The clear colorless contents were placed in a rotary evaporator and rotated at 37° C./300 Torr for 150 minutes, producing a damp residue and a distillate. The flask with the residue was immersed in a water bath at 45-50° C.; volatiles were distilled off at 10-20 Torr into a dry ice trap, giving 69 g distillate. The remaining dried solid was analyzed (APCI MS) and no evidence of alkylated DIPEA (m/e 212) was found, only protonated DIPEA (m/e 130). The trap contents were then fractionally distilled at atmospheric pressure. A forerun at 42-45° C. was discarded. A biphasic distillate (10.6 g) was then collected at 79-82° C. and analyzed (GCMS). The upper layer (0.6 g) was DIPEA and the lower layer (10 g) was the product FSO$_2$OCH$_2$CF$_3$ (lit bp=82-83° C. (King)).

These examples illustrate possible embodiments of the present invention. While various embodiments of the present invention have been described above, it should be understood that these are presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A method for preparing a fluorosulfonate salt, comprising:
reacting dissolved sulfuryl fluoride ($SO_2F_2$) with an alkoxide anion ($RO^-$) precursor in the presence of an aprotic base (B) without addition of water, wherein R is a primary alkyl or alkoxyalkyl group; and
isolating a resulting onium salt $[RB^+]$ $[FSO_3^-]$.

2. The method of claim 1, wherein the alkoxide anion ($RO^-$) precursor is a primary alcohol (ROH).

3. The method of claim 1, wherein the alkoxide anion ($RO^-$) precursor is a silyl ether having a formula $ROSiR"_3$, $(RO)_2SiR"_2$, $(RO)_3SiR"$ or $(RO)_4Si$, and R" is an alkyl group.

4. The method of claim 1, wherein the aprotic base (B) is a tertiary amine ($R'_3N$), wherein each R' is independently a $C_1$-$C_6$ alkyl or alkoxyalkyl, a cycloalkyl, morpholinyl, or bicycloalkyl group.

5. The method of claim 1, wherein the aprotic base is a heteroaromatic tertiary amine.

6. The method of claim 1, wherein the reaction is conducted at or below atmospheric pressure.

7. The method of claim 1, further comprising: isolating a resulting fluorosulfonate ester $ROSO_2F$.

8. The method of claim 7, wherein the alkoxide anion ($RO^-$) precursor is a hindered primary alkoxide.

9. The method of claim 7, wherein the aprotic base is a hindered base.

10. The method of claim 1, wherein the onium salt $[RB^+]$ $[FSO_3^-]$ is obtained by reacting a resulting fluorosulfonate ester $ROSO_2F$ with the aprotic base in situ or added subsequently.

11. The method of claim 1, wherein the onium salt $[RB^+]$ $[FSO_3^-]$ is a quaternary ammonium salt $[F SO_3]^-[RR'_3N]^+$, or a quaternary heteroaromatic salt $[FSO_3]^-[RNAr]^+$, wherein each R' is independently a $C_1$-$C_6$ alkyl or alkoxyalkyl, a cycloalkyl, morpholinyl, or bicycloalkyl group, and NAr is a heteroaromatic group.

12. A method for preparing a fluorosulfonate salt, comprising:
reacting dissolved sulfuryl fluoride ($SO_2F_2$) with an alcohol (ROH) in the presence of an aprotic base (B) under anhydrous condition, wherein R is a primary alkyl or alkoxyalkyl group; and
isolating a resulting onium salt $[RB^+]$ $[FSO_3^-]$.

13. The method of claim 12, wherein the alcohol (ROH) is a linear primary alcohol or alkoxyalcohol having from 1 to 20 carbon atoms.

14. The method of claim 12, wherein the alcohol (ROH) is selected from the group consisting of methanol, ethanol, n-propanol, n-butanol, n-pentanol, n-hexanol, 2-methoxyethanol, 3-methoxypropanol, 2-ethoxyethanol, and 3-ethoxypropanol, benzyl alcohol, a ring-substituted benzyl alcohol, 2-ethylhexanol and neopentanol.

15. The method of claim 12, wherein the alcohol (ROH) is partially or wholly fluorinated, except for the hydroxyl carbon.

16. The method of claim 12, wherein reacting sulfuryl fluoride ($SO_2F_2$) with an alcohol (ROH) is performed in a solvent, and the solvent is selected from the group consisting of dichloromethane, 1,1,1-trichloroethane, chloroform, tetrahydrofuran, acetonitrile, ethyl ether, chlorobenzene, fluorobenzene, 1,2-difluorobenzene, toluene, n-propyl ether, isopropyl ether, di-n-butyl ether and methyl tert-butyl ether.

17. The method of claim 12, wherein the molar ratio of the aprotic base (B) to the alcohol (ROH) is 2:1 or greater, and the molar ratio of $SO_2F_2$ to ROH is 1:1 or greater.

18. The method of claim 12, further comprising isolating a resulting fluorosulfonate ester ($ROSO_2F$), and where the alcohol (ROH) is a hindered primary alcohol, or the aprotic base is a hindered base.

19. The method of claim 12, wherein the aprotic base comprises a tertiary amine ($R'_3N$) or a heteroaromatic tertiary amine (:NAr), wherein each R' is independently a $C_1$-$C_6$ alkyl or alkoxyalkyl, a cycloalkyl, morpholinyl, or bicycloalkyl group.

20. The method of claim 12, wherein the resulting onium salt $[RB^+]$ $[FSO_3^-]$ is a quaternary ammonium salt $[F SO_3]^-[RR'_3N]^+$, or a quaternary heteroaromatic salt $[FSO_3]^-[RNAr]^+$, wherein each R' is independently a $C_1$-$C_6$ alkyl or alkoxyalkyl, a cycloalkyl, morpholinyl, or bicycloalkyl.

21. The method of claim 12, wherein the aprotic base comprises a tertiary amine ($R'_3N$), and the resulting onium salt is a quaternary ammonium salt $[FSO_3]^-[RR'_3N]^+$.

22. A method for preparing a fluorosulfonate salt, comprising:
reacting dissolved sulfuryl fluoride ($SO_2F_2$) with a silyl ether, optionally in the presence of an aprotic base (B), wherein the sily ether has a formula $ROSiR"_3$ or $(RO)_2SiR"_2$, $(RO)_3SiR"$ or $(RO)_4Si$, R is a primary alkyl or alkoxyalkyl group and R" is an alkyl group; and
isolating a resulting onium salt $[RB^+]$ $[FSO_3^-]$.

23. The method of claim 22, wherein R" is methyl or ethyl group.

24. The method of claim 22, wherein the aprotic base comprises a tertiary amine ($R'_3N$), and the resulting onium salt is a quaternary ammonium salt $[FSO_3]^-[RR'_3N]^+$, wherein each R' is independently a $C_1$-$C_6$ alkyl or alkoxyalkyl, a cycloalkyl, morpholinyl, or bicycloalkyl group.

25. The method of claim 22, further comprising isolating a resulting fluorosulfonate ester ($ROSO_2F$).

26. The method of claim 22, wherein the resulting onium salt $[RB^+]$ $[FSO_3^-]$ is obtained by reacting a resulting fluorosulfonate ester ($ROSO_2F$) with the aprotic base in situ or added subsequently.

27. The method of any of claims 1, 12 and 22, comprising adding a protic amine to generate fluoride ion by reaction with $SO_2F_2$.

28. The method of any of claims 1, 12 and 22, wherein a fluorosulfonate ester is produced as a stable ester, and is treated with a protic amine to provide the resulting onium salt.

* * * * *